United States Patent [19]

Pesa et al.

[11] 4,356,124
[45] Oct. 26, 1982

[54] PROCESS FOR THE PRODUCTION OF PYRROLIDONES

[75] Inventors: Frederick A. Pesa, Aurora; Anne M. Graham, Northfield, both of Ohio

[73] Assignee: The Standard Oil Company, Cleveland, Ohio

[21] Appl. No.: 82,192

[22] Filed: Oct. 5, 1979

[51] Int. Cl.$^3$ .................. C07D 207/38; C07D 207/40
[52] U.S. Cl. ................ 260/326.5 FN; 260/326.5 FL; 260/326.5 FM
[58] Field of Search ............. 260/326.5 FN, 326.5 FL

[56] References Cited

U.S. PATENT DOCUMENTS

| | | | |
|---|---|---|---|
| 3,080,377 | 3/1963 | Liao | 260/326.5 FN |
| 3,092,638 | 6/1963 | Liao et al. | 260/326.5 FN |
| 3,095,423 | 6/1963 | Copenhaver et al. | 260/326.5 FN |
| 3,198,808 | 8/1965 | Himmele et al. | 260/326.5 FN |
| 3,448,118 | 6/1969 | Chichery et al. | 260/326.5 FN |
| 3,812,149 | 5/1974 | Hollstein | 260/326.5 FN |
| 4,042,599 | 8/1977 | Greene | 260/326.5 FN |
| 4,263,175 | 4/1981 | Pesa et al. | 252/472 |

FOREIGN PATENT DOCUMENTS 580034  7/1959  Canada ..................... 260/326.5 FN

*Primary Examiner*—Donald G. Daus
*Assistant Examiner*—D. B. Springer
*Attorney, Agent, or Firm*—Salvatore P. Pace; Herbert D. Knudsen; Larry W. Evans

[57] ABSTRACT

Five-membered nitrogen-containing saturated heterocyclic compounds, e.g. pyrrolidone, can be prepared by the catalytic hydrogenation/amination of a five-membered heterocyclic anhydride or the corresponding acid. This reaction proceeds with high yields and selectivities when it is conducted in the presence of complex catalysts containing ruthenium.

17 Claims, No Drawings

PROCESS FOR THE PRODUCTION OF PYRROLIDONES

BACKGROUND OF THE INVENTION

Five-membered nitrogen-containing saturated heterocyclic compounds, e.g. pyrrolidone, are particularly useful as intermediates in the preparation of nylon-4 type polymers. These compounds are also useful in the preparation of n-methyl pyrrolidone and n-vinyl pyrrolidone which can be used as organic solvents.

The production of pyrrolidone from maleic anhydride is known. For example, U.S. Pat. No. 3,109,005, discloses a process wherein a mixture of maleic anhydride, dioxane and Raney nickel are charged to a reactor at a temperature of 250° C. and a pressure of 200 atmospheres for about 10 hours. Moreover, Japanese Pat. No. 71/37,590 discloses a process wherein maleic anhydride is hydrogenated in dioxane at below 100° C. at 145 atmospheres in the presence of a supported cobalt nickel catalyst. Ammonia is then added to the reaction vessel and the temperature is increased to 250° C. to produce pyrrolidone.

The prior art methods for producing pyrrolidone are each disadvantageous for various reasons. First, these reactions required very high temperatures and pressures. Second, some of the prior art processes are two-step processes. Third, long reaction times are necessary. The instant process, on the other hand, can be conducted continuously in a single step at moderate temperatures and pressures to produce pyrrolidone from maleic anhydride. Furthermore, the instant process results in high yields and selectivities of pyrrolidone.

SUMMARY OF THE INVENTION

The instant invention provides a process for producing a five-membered saturated nitrogen-containing heterocyclic compound by contacting hydrogen, an amine and at least one five-member oxygen-containing heteroclycic anhydride or the corresponding acid in the presence of an oxide complex catalyst containing ruthenium.

More specifically, this invention provides a process for the production of pyrrolidone, said process comprising contacting hydrogen, aqueous ammonia and maleic anhydride in the presence of an oxide complex catalyst containing ruthenium, iron and nickel or cobalt.

In an alternate embodiment, the invention provides a catalyst composition comprising an oxide complex of the formula:

$$A_a D_b Fe_c Ru_d O_x$$

wherein
A is Ni, Co or mixtures thereof;
D is selected from the group consisting of Rh, Pd, Os, Ir, Pt, Zn and mixtures thereof; and
wherein
a, c and d are 0.01 to 1;
b is 0 to 1; and
x represents the number of oxygens required to satisfy the valence requirements of the other elements present in the catalyst.

DETAILED DESCRIPTION

Reactants

Generally, any five-membered oxygen-containing heterocyclic anhydride or corresponding acid can be employed as a reactant in the inventive process. However, steric hindrance may become a factor and the reaction rate may be reduced if this reactant is substituted with one or more bulky groups.

Preferred heterocyclic anhydrides or corresponding acids which are useful in the instant process have the following structures:

Anhydrides

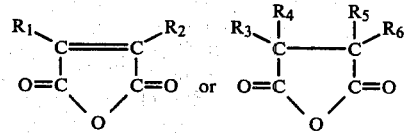

Corresponding Acids

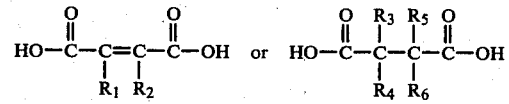

wherein $R_1$, $R_2$, $R_3$, $R_4$, $R_5$ and $R_6$ are each independently selected from the group consisting of:
(1) hydrogen; and
(2) $C_{1-4}$ alkyls.

Preferably, $R_1$, $R_2$, $R_3$, $R_4$, $R_5$ and $R_6$ are each independently selected from:
(1) hydrogen;
(2) $C_{1-2}$ alkyl.

Most preferably $R_1$, $R_2$, $R_3$, $R_4$, $R_5$ and $R_6$ are each hydrogen.

Examples of reactants which are within the scope of this invention are maleic anhydride and succinic anhydride and the corresponding acids.

A wide variety of amines are also useable in the instant process. These amines all have the following formula:

$$\begin{array}{c} R_7 \\ | \\ N-H \\ | \\ H \end{array}$$

wherein $R_7$ is selected from the group consisting of:
(1) hydrogen;
(2) $C_{1-4}$ alkyl;
(3) aryl;
(4) $-(CH_2)_q-OH$, wherein q is 1 to 4.

Preferably, $R_7$ is selected from the group consisting of hydrogen and methyl.

The ratio of the reactants, i.e. heterocyclic anhydride or corresponding acid, amine and hydrogen, charged to the reactor in this process is not critical. The reaction will proceed as long as some of each of these reactants is present in the reaction system. However, it is preferred to conduct the reaction in the presence of an excess of hydrogen and amine. Generally, this reaction is conducted with about 3 to 20 moles of hydrogen per mole of heterocyclic anhydride and from about 1 to 5 moles of amine per mole of heterocyclic anhydride. These reactants can be added separately to the reaction zone or two or more of these reactants may be combined prior to entering the reaction zone.

If desired, a carrier which is inert to the reactants, products and catalyst can be included within the reaction system. Suitable carriers include water and dioxane.

PROCESS CONDITIONS

In carrying out the inventive process, the heterocyclic anhydride or corresponding acid, hydrogen, and an amine are contacted in the presence of the catalyst described below for effecting the hydrogenation/amination reaction. The process of this invention may be conducted using various techniques and reactors, and both batch type and continuous operations are contemplated. Additionally, recycle of the reaction product to the reaction mixture may be beneficial to the reaction. In a preferred preparation, aqueous ammonia and the heterocyclic anhydride in the desired concentrations are contacted with hydrogen over the catalyst in a continuous manner.

The reaction temperature may range from about 100° C. to 400° C., but preferably temperatures within the range of from about 100° C. to 300° C. are employed. The reaction is continued at the desired temperature for a period of time ranging from about 0.1 to 5 hours, however, with continuous operation the contact time may be as low as 0.01 hours.

While the reaction may be carried out using pressures ranging from about 500 to 5,000 psi, one of the more important advantages associated with this process is that optimum results are obtained at much lower pressures than are employed in the processes of the prior art. The use of lower pressures in the instant process minimizes side reactions and has the important economic significance of requiring less expensive reactor equipment. Preferably, hydrogen pressures of about 1,000 psi are employed.

CATALYSTS

Any catalyst containing ruthenium oxide may be employed in the instant process. The oxide complex catalysts which are particularly useful in this invention can be represented by the following formula:

$$A_aD_bFe_cRu_dO_x$$

wherein
A is selected from the group consisting of nickel, cobalt and mixtures thereof;
D is selected from the group consisting of Rh, Pd, Os, Ir, Pt, Zn, and mixtures thereof; and
wherein
a, b and c are each independently 0 to 1; with the proviso that a and c cannot both be equal to 0;
d is 0.01 to 1; and
x represents the number of oxygens required to satisfy the valence requirements of the other elements present in the catalyst.

This oxide complex catalyst can be any catalyst delineated by the general formula above with respect to the components of the catalyst. Preferred are those catalysts wherein A is nickel and both a and c are 0.01 to 1.

The exact chemical nature of this oxide complex catalyst is not known. This catalyst may be a mixture of oxides, for example, or an oxide complex of all the contained elements. In any event, this type of catalyst is generally known in the art.

The oxide complex catalyst can be made by techniques which are essentially the same as those techniques described in the art for other oxidation catalysts. (See U.S. Pat. No. 3,642,930, which is herein incorporated by reference.) Even though there are numerous techniques that may be utilized to give acceptable oxide complex catalysts, some of the preferred methods of making these catalysts are described below.

These catalysts can be prepared from any mixture of compounds that can give the desired oxide components. Preferably, the catalyst is prepared by coprecipitating decomposable salts such as nitrates, acetates, halides and/or oxides. These catalysts are effective in both the calcined and uncalcined form. Reduction or partial reduction of the complexed catalyst with hydrogen before reaction is preferred. Since the presence of Na+ and Cl− ions in the catalyst seems to decrease the yield, it is preferable to use catalyst preparation techniques wherein no Na+ or Cl− can be incorporated into the catalyst.

These catalysts can be used in the supported, unsupported or coated form. Preferred support materials are silica, $ZrO_2$, alumina, phosphates, silica alumina and zeolites. Any other known support material can be used which is stable under the reaction conditions to be encountered in the use of the catalyst. In the supported form, the support preferably comprises 5% to 95% by weight of the catalyst, preferably 10% to 60% by weight of the catalyst. In the coated catalyst form the inert material is preferably in the range of from about 20% to 99% by weight of the catalyst.

RECOVERY

The reaction product obtained upon completion of the reaction is normally in the vapor phase. This reaction product can be subjected to suitable known separation techniques, e.g. condensation followed by solvent extraction or fractional distillation, to yield the desired end product.

SPECIFIC EMBODIMENTS

In order to more thoroughly illustrate the present invention, the following working examples are presented. In these examples, conversions and yields are defined as follows:

$$\text{Conv.} = \frac{\text{Moles Heterocyclic Anhydride Reacted}}{\text{Moles Heterocyclic Anhydride Fed}} \times 100$$

$$\text{Yield} = \frac{\text{Moles Product}}{\text{Moles Heterocyclic Anhydride Fed}} \times 100$$

Examples were performed as follows:

EXAMPLE 1

A catalyst comprising 30% $RuFeO_x$ on $SiO_x$ was prepared as follows. First, 18.68 grams of $RuCl_3.14H_2O$ and 21.62 grams of $FeCl_3.6H_2O$ were dissolved in 300 ml. of water and stirred for 30 minutes. A 50% NaOH and water solution was added dropwise with constant stirring to bring the pH up to 8.6 and to precipitate the oxides. The slurry was stirred and heated near boiling for 30 minutes, cooled, filtered and washed thoroughly. The resulting mixed oxide was dried overnight at 125° C. and calcined for 3 hours at 350° C., and then ground to pass 140 mesh.

Next, 15 grams of the above oxide were slurried in 50 ml. of water. To this solution was added 87.5 grams of Nalco silica solution (40% solids). The mixture was heated and stirred until it reached the consistency of toothpaste. The catalyst was then dried overnight at 125° C., calcined for 3 hours at 350° C. and ground to 10/40 mesh.

A fixed-bed reactor was packed with 40 cc. of the above catalyst, and the system was charged to the desired pressure. Hydrogen was allowed to pass over the catalyst at 150 cc. per minute while the reactor was heated to the reaction temperature in stages. The system was then left to pre-reduce and equilibrate, under $H_2$ flow, for 2 hours.

The liquid feed, 10% maleic anhydride in water with 2 moles of ammonia per mole of maleic anhydride, was pumped in at 20 cc. per hour. The product was then condensed in a separate cooled receiver for 1 hour. At the completion of the collection run, the product was analyzed for pyrrolidone. The results are shown in Table I.

EXAMPLE 2

A catalyst comprising 18% $RuFeO_x$ on $Al_2O_3$ with 10% $SiO_2$ was prepared as follows. first, a mixed oxide $RuFeO_x$ catalyst was prepared as shown above. 15 grams of this mixed oxide and 60 grams of $Al_2O_3$ powder were slurried in 150 ml. of water. This mixture was evaporated with stirring to the consistency of toothpaste. The catalyst was then dried at 125° C. overnight. The resulting fine powder was reslurried in 100 ml. of water and 20.75 grams Nalco silica solution (40% solids). This slurry was evaporated and dried overnight at 125° C., calcined for 3 hours at 350° C. and ground to 10/40 mesh.

This catalyst was placed in the experimental setup disclosed in Example 1. The results are shown in Table I.

EXAMPLE 3

A catalyst comprising 5% $RuFeO_x$ on $Al_2O_3$ was prepared by the above method and placed into the experimental apparatus. The results are shown in Table I.

EXAMPLE 4

A mixed metal oxide comprising $RuFeNiO_x$ was prepared as shown in Example 1 using 7.01 grams of $RuCl_3.14H_2O$ and 8.11 grams of $FeCl_3.6H_2O$ and $NiCl_2.H_2O$. Next, 50 grams of Norton SA 5223 Alundum, 10/30 mesh, were placed in a pint glass jar. 5.4 grams of water were sprayed onto the Alundum in two portions, and the jar was rolled on a ballmiller for 10 minutes after each addition. 1.4 grams of the mixed metal oxide were added and the jar was then rolled on a ballmiller for 15 minutes. This last step, addition of 1.4 grams of mixed metal oxide, was repeated. The coated catalyst was dried overnight at 125° C. and calcined for 3 hours at 350° C.

This catalyst was then placed in the experimental apparatus discussed in Example 1 and the results are shown in Table I.

EXAMPLES 5 THRU 7

Catalysts comprising $RuFeCoO_x$, $RuFePdO_x$ and $RuZnNiO_x$ were coated on Alundum. These catalysts were prepared by the method shown in Example 4 and were placed in the experimental apparatus shown in Example 1. The results are tabulated in Table I.

TABLE I

Hydrogenation/Amination of Maleic Anhydride in the Presence of Various Catalysts Temperature: 250° C.
Pressure: 1,000 psi

| Example | Catalyst | Conv. (%) | Yield (%) |
|---|---|---|---|
| 1 | 30% $RuFeO_x$ on $SiO_2$ | 100.0 | 20.1 |
| 2 | 20% $RuFeO_x$ on 90% $Al_2O_3$ and 10% $SiO_2$ | 83.7 | 45.2 |
| 3 | 5% $RuFeO_x$ on $Al_2O_3$ | 89.8 | 41.5 |
| 4 | $RuFeNiO_x$ | 81.3 | 77.3 |
| 5 | $RuFeCoO_x$ | 99.0 | 39.1 |
| 6 | $RuFePdO_x$ | 100.0 | 32.8 |
| 7 | $RuZnNiO_x$ | 100.0 | 61.4 |

EXAMPLES 8 THRU 14

A catalyst comprising $RuFeNiO_x$ was prepared as shown in Example 4 and placed into the experimental apparatus disclosed in Example 1. The process parameters of this process were varied as shown in Table II. The yield of pyrrolidone obtained in these examples is also shown in Table II.

TABLE II

Hydrogenation/Amination of Maleic Anhydride

Catalyst: $RuFeNiO_x$
Liquid Feed: 10% MAH (2:1 $NH_3$/MAH)

| Example | Temperature (°C.) | Pressure (psi) | $H_2$ Flow Rate (cc/min) | Liquid Flow Rate (cc/min) | Conversion (%) | Yield (%) |
|---|---|---|---|---|---|---|
| 8 | 250 | 1,000 | 150 | 20 | 81.3 | 77.3 |
| 9 | 200 | 1,000 | 150 | 20 | 100.0 | 19.2 |
| 10 | 250 | 500 | 150 | 20 | 100.0 | 15.8 |
| 11 | 250 | 1,000 | 300 | 40 | 100.0 | 61.8 |
| 12 | 250 | 1,000 | 300 | 20 | 98.0 | 43.1 |
| 13 | 250 | 1,000 | 75 | 20 | 99.0 | 69.7 |
| 14 | 250 | 1,200 | 150 | 20 | 97.0 | 51.9 |

Although only a few embodiments of the present invention have been specifically described above, it should be appreciated that many additions and modifications can be made without departing from the spirit and scope of the invention. These and all other modifications are intended to be included within the scope of the present invention, which is to be limited only by the following claims:

We claim:

1. A process for producing a five-membered saturated action comprising the step of contracting hydrogen, an amine and a five-membered oxygen-containing heterocyclic anhydride or the corresponding acid in the presence of an oxide complex catalyst represented by the formula:

$$A_a D_b Fe_c Ru_d O_x$$

wherein
  A is cobalt, nickel, or mixtures thereof; and
  D is selected from the group consisting of Rh, Pd, Os, Ir, Pt, and Zn; and
wherein
  a, b and c are each independently 0 to 1; with the proviso that a and c are not both equal to 0;
  d is 0.01 to 1; and x represents the number of oxygens required to satisfy the valence requirements of the other elements present in the catalyst;

wherein the heterocyclic anhydride or corresponding acid is represented by the formulas:

Anhydrides

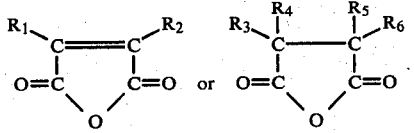

Corresponding Acids

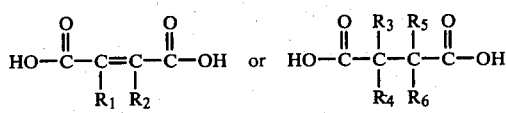

wherein $R_1$, $R_2$, $R_3$, $R_4$, $R_5$ and $R_6$ are each independently selected from the group consisting of:
(1) hydrogen;
(2) $C_{1-4}$ alkyls and wherein ammonia or amine is represented by the following formula:

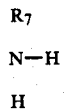

wherein $R_7$ is selected from the group consisting of:
(1) hydrogen;
(2) $C_{1-4}$ alkyl;
(3) aryl; and
(4) —$(CH_2)_q$—OH, wherein q is 1 to 4.

2. The process of claim 1 wherein $R_1$, $R_2$, $R_3$, $R_4$, $R_5$ and $R_6$ are hydrogen.

3. The process of claim 1 wherein $R_7$ is hydrogen or methyl.

4. The process of claim 1 wherein the ratio of hydrogen to the heterocyclic anhydride or corresponding acid is 3-20:1.

5. The process of claim 1 wherein the pressure is maintained at about 1,000 psi.

6. The process of claim 1 wherein A is nickel.

7. The process of claim 1 wherein c is greater than 0.

8. The process of claim 1 wherein a is greater than 0.

9. The process of claim 1 wherein b is greater than 0.

10. The process of claim 1 wherein the catalyst is an oxide complex containing Ru, Fe and Ni.

11. The process of claim 1 wherein said process is a single step process.

12. The process of claim 1 wherein the anhydride is maleic anhydride and wherein the nitrogen-containing heterocyclic compound produced is pyrrolidone.

13. The process of claim 1 wherein both a and c are 0.01 to 1.

14. The process of claim 13 wherein A is nickel.

15. The process of claim 13 wherein A is cobalt.

16. The process of claim 13 wherein b is greater than 0.

17. The process of claim 1 wherein said nitrogen-containing heterocyclic compound is a lactam.

* * * * *

UNITED STATES PATENT AND TRADEMARK OFFICE
CERTIFICATE OF CORRECTION

PATENT NO. : 4,356,124
DATED : October 26, 1982
INVENTOR(S) : F. A. Pesa, A. M. Graham It is certified that error appears in the above-identified patent and that said Letters Patent is hereby corrected as shown below:

Claim 1, line 2, "action" should read --lactam-- and "contracting" should read --contacting--.
Delete claim 17.

On the title page, "17 claims", should read --16 claims--.

Signed and Sealed this

Eighth Day of February 1983

[SEAL]

Attest:

GERALD J. MOSSINGHOFF

Attesting Officer

Commissioner of Patents and Trademarks